United States Patent
Verbakel et al.

(10) Patent No.: US 9,753,156 B2
(45) Date of Patent: Sep. 5, 2017

(54) DETECTOR

(71) Applicant: KONINKLIJKE PHILIPS N.V., Eindhoven (NL)

(72) Inventors: Frank Verbakel, Helmond (NL); Klaus Juergen Engel, Veldhoven (NL); Antonius Johannes Maria Nellissen, Horst (NL); Herfried Karl Wieczorek, Aachen (DE); Eric Cornelius Egbertus Van Grunsven, Someren (NL); Ira Micah Blevis, Zichron Yaakov (IL); Roger Steadman Booker, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/768,231

(22) PCT Filed: Feb. 28, 2014

(86) PCT No.: PCT/IB2014/059334
§ 371 (c)(1),
(2) Date: Aug. 17, 2015

(87) PCT Pub. No.: WO2014/132232
PCT Pub. Date: Sep. 4, 2014

(65) Prior Publication Data
US 2015/0362604 A1    Dec. 17, 2015

Related U.S. Application Data

(60) Provisional application No. 61/771,279, filed on Mar. 1, 2013.

(51) Int. Cl.
*G01T 1/24* (2006.01)
*G01N 23/02* (2006.01)

(52) U.S. Cl.
CPC ............. *G01T 1/244* (2013.01); *G01N 23/02* (2013.01); *G01T 1/24* (2013.01)

(58) Field of Classification Search
CPC .................................. G01T 1/24; G01T 1/244
See application file for complete search history.

(56) References Cited

U.S. PATENT DOCUMENTS

| 5,248,885 A | 9/1993 | Sato et al. |
| 5,510,626 A * | 4/1996 | Nelson et al. ............. 250/591 |

(Continued)

FOREIGN PATENT DOCUMENTS

| EP | 0473125 A2 | 3/1992 |
| WO | 2012153210 A2 | 11/2012 |

OTHER PUBLICATIONS

Bale, D. S., et al.; Nature of polarization in wide-bandgap semiconductor detectors under high-flux irradiation: Application to semi-insulating Cd1—xZnxTe; 2008; Physical Review; B:77:035205-1--035205-16.

(Continued)

*Primary Examiner* — David Porta
*Assistant Examiner* — Hugh H Maupin

(57) ABSTRACT

The invention relates to a detector (6) for detecting radiation, especially x-ray radiation used in a computed tomography system. The detector comprises a direct conversion material (9) for converting radiation into electrons and holes, which are used for generating an electrical detection signal. The direct conversion material is illuminated with illumination light being broadband visible and/or broadband infrared light for reducing, in particular, eliminating, a polarization of the direct conversion material, which may occur when being traversed by the radiation to be detected and which may reduce the detection performance. By reducing the (Continued)

polarization of the direct conversion material the detection performance can be improved.

13 Claims, 7 Drawing Sheets

(56) References Cited

U.S. PATENT DOCUMENTS

| | | | |
|---|---|---|---|
| 5,563,421 | A | 10/1996 | Lee et al. |
| 7,312,458 | B2 | 12/2007 | Blevis |
| 8,927,937 | B2 | 1/2015 | Schwarzman et al. |
| 2007/0201616 | A1* | 8/2007 | Rowlands ............ G02F 1/1354 378/98.2 |
| 2010/0078559 | A1 | 4/2010 | Szeles et al. |
| 2010/0086098 | A1 | 4/2010 | Shahar et al. |
| 2012/0068078 | A1 | 3/2012 | Zhang et al. |
| 2013/0108019 | A1* | 5/2013 | Tkaczyk ................ A61B 6/037 378/62 |
| 2013/0193336 | A1* | 8/2013 | Washington et al. .... 250/370.13 |

OTHER PUBLICATIONS

Del Sordo, S., et al.; Progress in the Development of CdTe and CdZnTe Semiconductor Radiation Detectors for Astrophysical and Medical Applications; 2009; Sensors; 9:2491-3526.

Grill, R., et al.; Polarization Study of Defect Structure of CdTe Radiation Detectors; 2011; IEEE Trans. on Nuclear Science; 58(6)3172-3181.

Nemirovsky, Y., et al.; Recent progress in n-type CdZnTe arrays for gamma-ray spectroscopy; 2001; Proc. 11th Intl. Workshop on Room Temperature Semiconductor X- and Gamma-Ray Detectors and Associated Electronics; 458(1-2) 325-333.

* cited by examiner

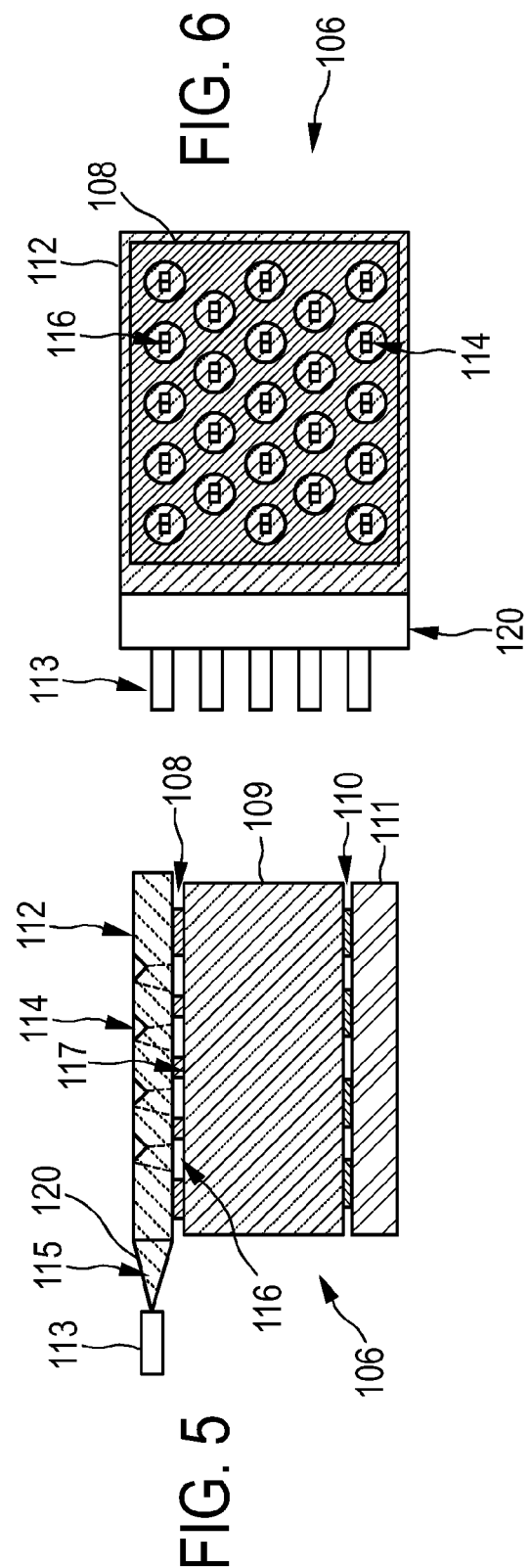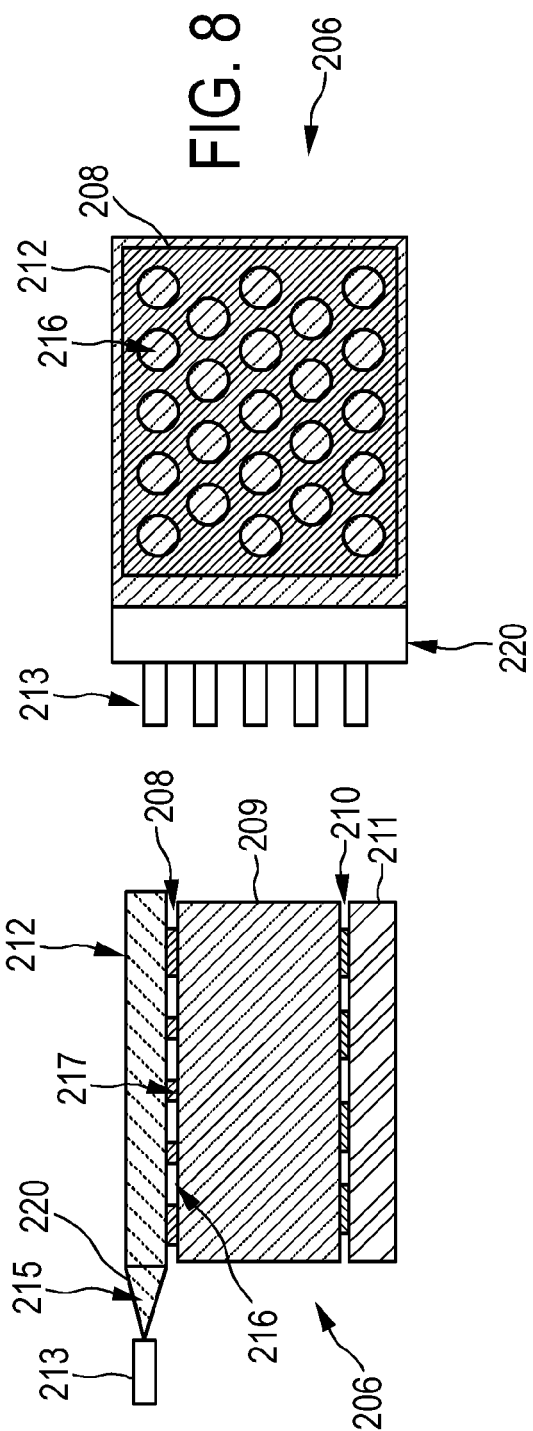

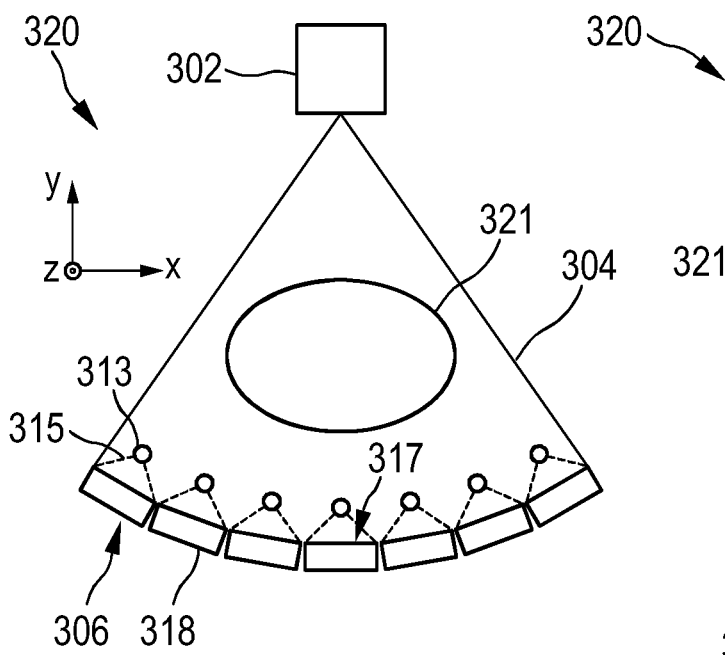
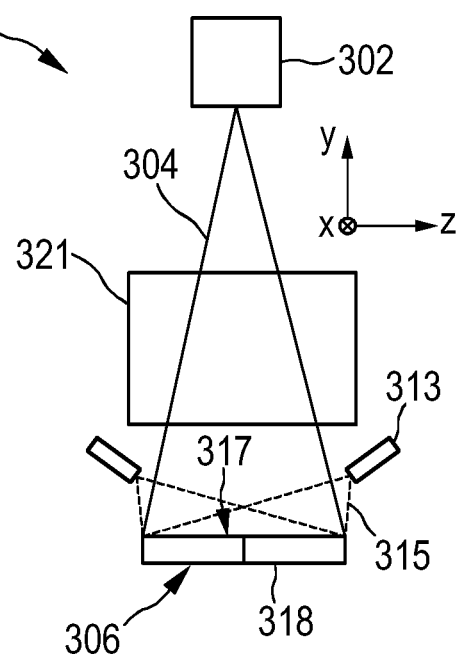
FIG. 9  FIG. 10
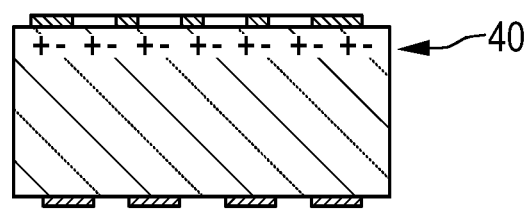
FIG. 11

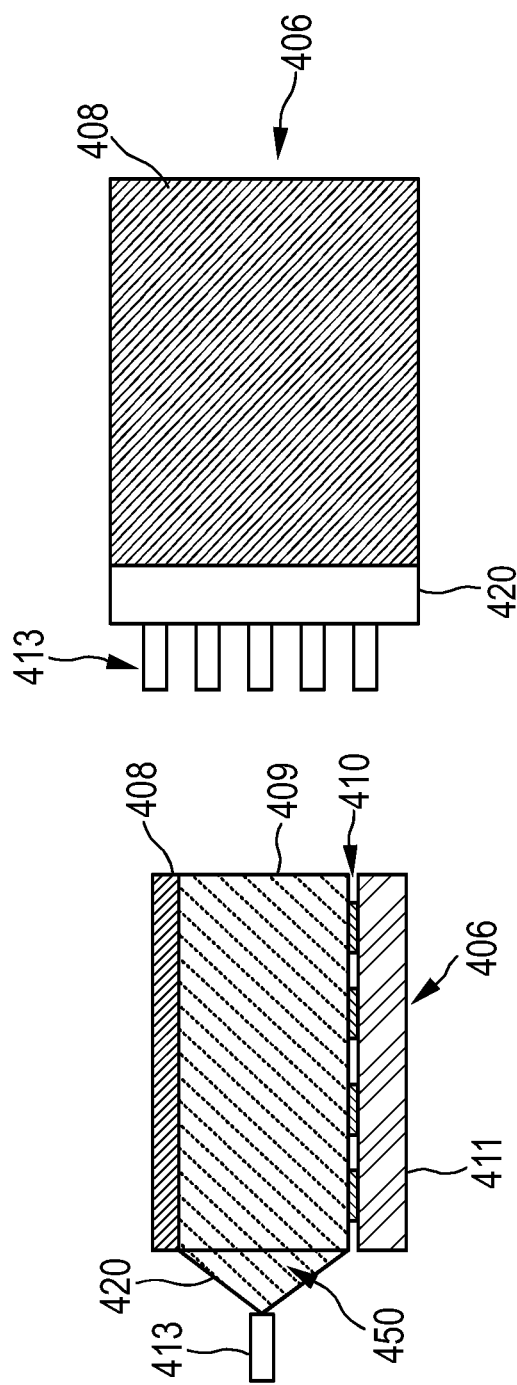

DETECTOR

CROSS REFERENCE TO RELATED APPLICATIONS

This application is a national filing of PCT application Ser. No. PCT/IB2014/059334, filed Feb. 28, 2014, published as WO 2014/132232 A2 on Sep. 4, 2014, which claims the benefit of US. provisional application Ser. No. 61/771,279 filed Mar. 1, 2013, which is incorporated herein by reference.

FIELD OF THE INVENTION

The invention relates to a detector, a detection method and a detection computer program for detecting radiation, in particular, for detecting x-ray radiation or gamma radiation. The invention relates further to a projection data generation system, a projection data generation method and a projection data generation computer program for generating projection data of an object.

BACKGROUND OF THE INVENTION

US 2010/0086098 A1 discloses a photon counting CdZnTe (CZT) pixelated detector comprising an anode, a cathode and a CZT crystal between the anode and the cathode for converting x-ray radiation into electrons and holes, wherein the electrons are collected by the anode and a detection signal is generated depending on the collected electrons. The performance of the detector is critically affected by a charging of the CZT crystal, which leads to an internal electrical field counteracting a bias voltage applied to the anode and the cathode. This polarization of the detector is reduced by using infrared light having one or more specific wavelengths.

SUMMARY OF THE INVENTION

It is an object of the present invention to provide a detector, a detection method and a detection computer program, which allow for an improved reduction of polarization. It is a further object of the present invention to provide a projection data generation system, a projection data generation method and a projection data generation computer program for generating projection data of an object by using the detector. In a first aspect of the present invention a detector for detecting radiation is presented, wherein the detector comprises:

an anode, a cathode and an intermediate direct conversion material for converting radiation into electrons and holes, wherein the electrons are collectable by the anode,
a detection signal generator for generating a detection signal depending on the collected electrons,
an illuminator for illuminating the direct conversion material with illumination light being broadband visible and/or broadband infrared light.

Since the illuminator illuminates the direct conversion material not with only one or several specific wavelengths of infrared light, but with, for instance, illumination light being broadband infrared light, trapped holes can be directly excited at different trap levels. This leads to a faster movement of holes that normally move relatively slowly due to trapping and detrapping actions. They can therefore move more quickly out of the direct conversion material such that the net accumulation of hole charge in the direct conversion material and thus the polarization can be reduced, in particular eliminated or prevented. Moreover, the broadband infrared illumination light can be such that the direct conversion material is heated, which can also lead to a reduced polarization, in particular, an elimination or prevention of the polarization. If broadband visible light is used, the illumination light creates electrons which migrate to the trapped holes, where the polarization can be reduced, in particular, eliminated, by recombination of the electrons and holes.

The direct conversion material is preferentially a direct conversion crystal like a CdTe crystal or a CZT crystal. The direct conversion material is preferentially adapted to convert x-ray radiation and/or gamma radiation into electrons and holes.

It is preferred that the illuminator and the cathode are adapted such that the direct conversion material is illuminated through the cathode with the illumination light. The cathode may be made of a cathode material being transparent to the illumination light and/or it may comprise openings, through which the direct conversion material is illuminatable by the illumination light.

The light source and the cathode are preferentially adapted such that the direct conversion material is homogenously illuminated. For providing a substantially homogenous illumination the illuminator may comprise a light source for providing the illumination light and a light guiding element for guiding the illumination light such that the direct conversion material is substantially homogenously illuminated through the cathode by the illumination light. The light guiding element may be a light distribution element being a diffusing and/or a diffractive element for diffusing and/or diffracting the illumination light before traversing the cathode. In particular, the light distribution element may be a diffractive and/or diffusing plate, into which the illumination light of the light source can be coupled and from which the illumination light can be coupled out substantially homogenously. Preferentially, the light distribution element is arranged on the cathode.

The direct conversion material preferentially comprises an incidence surface, through which the radiation to be detected enters the direct conversion material, wherein the illuminator comprises a light source for providing the illumination light, wherein the light distribution element and the light source are adapted such that the illumination light is coupled into the light distribution element and the light source is arranged laterally from the incidence surface such that the light source does not prevent the radiation to be detected from reaching the direct conversion material, wherein the light distribution element comprises optical structures for coupling light out of the light distribution element towards the cathode, wherein the cathode comprises openings and wherein the light distribution element and the cathode are adapted such that the optical structures of the light distribution element and the openings of the cathode are aligned with each other. The openings and the optical structures are preferentially homogeneously distributed along the incidence surface such that a substantially homogeneous illumination of the direct conversion material by the illumination light can be provided.

In a further embodiment the direct conversion material comprises an incidence surface, through which the radiation to be detected enters the direct conversion material, wherein the cathode is arranged on the incidence surface and wherein the illuminator is adapted such that the direct conversion material is illuminated by the illumination light in an illumination direction being inclined with respect to the incidence surface. Thus, in this embodiment the illumination direction is not parallel and not perpendicular to the incidence surface. Moreover, in this embodiment the illuminator may comprise at least two light sources for illuminating the incidence surface from different illumination directions. For instance, it can be illuminated from two opposing sides of the detector. This allows illuminating the direct conversion material by the illumination light, without necessarily having to arrange parts of the illuminator on the incidence surface. The illuminator can therefore be constructed, without considering an interaction with the radiation to be detected, in particular, with x-ray radiation or gamma radiation.

In a further preferred embodiment the direct conversion material comprises an incidence surface, through which the radiation enters the direct conversion material, wherein the cathode is arranged on the incidence surface and wherein the illuminator comprises a light source, which is transparent to the radiation to be detected, on the cathode. Moreover, the light source preferentially comprises at least two electrodes and an intermediate light emitting material, wherein the light emitting material is adapted such that it emits light, if a voltage is applied to the at least two electrodes, wherein one of the electrodes of the light source is formed by the cathode on the incidence surface. The light source is preferentially an organic light emitting device (OLED) or another light emitting device. This allows for a very compact construction of the detector including the illuminator.

In a further embodiment the illuminator is a separate element such that it is movable with respect to the anode, the cathode and the direct conversion material. This separation is especially useful, if the detector is used by a projection data generation system for generating projection data of an object, wherein the system comprises a radiation source for providing radiation for traversing the object and the detector for detecting the radiation, after having traversed the object, and for generating a detection signal depending on the detected radiation, wherein the projection data are generated based on the generated detection signal, and wherein the system further comprises a rotor and a stator, wherein the rotor is rotatable with respect to the stator. In this example, the radiation source, the anode, the cathode and the direct conversion material of the detector can be mounted on the rotor and the separate illuminator of the detector can be mounted on the stator, wherein the illuminator can be adapted to illuminate an entire circular region of the projection data generation system, through which the cathode is moved while being rotated. It may therefore not be necessary to rotate the illuminator together with the detector, which can simplify the construction of the detector on the rotor.

In a preferred embodiment, the illuminator is adapted to illuminate the direct conversion material in an intensity modulated mode, particularly a pulsed mode. Moreover, the illuminator and the detection signal generator may be adapted such that at a time either the direct conversion material is illuminated by the light or a detection signal is generated. This can reduce a generally possible adverse effect of the illumination light on the generated detection signal. In particular, pulsed illumination light and the detection of the radiation, for instance, of the x-ray radiation or the gamma radiation, can be synchronized such that the generated detection signal does not have any contribution from the illumination light, thereby improving the quality of the detection signal. In another embodiment the illuminator can be adapted to illuminate the direct conversion material in a continuous mode.

The illuminator may be adapted to illuminate the direct conversion material depending on the generated detection signal. For instance, the illuminator can be adapted to illuminate the direct conversion material in a pulsed mode, wherein the illuminator can be adapted such that the time of illuminating the direct conversion material by a light pulse and/or the intensity of the light pulse depends on the generated detection signal. In particular, the illuminator can be adapted to increase the pulse frequency with increasing x-ray intensity as indicated by the detection signal. This control of the illumination of the direct conversion material by the illumination light depending on the generated detection signal can lead to an improved illumination by the illumination light. The illuminator can also be adapted to illuminate the direct conversion material depending on the radiation emitted by a radiation source, for instance, of an x-ray radiation source or a nuclear radiation source. The radiation source may provide a signal to the detector being indicative of the, for instance, radiation flux, wherein the illuminator can be adapted to illuminate the direct conversion material depending on the radiation flux. The dependence of the illumination on the signal provided by the radiation source and/or the generated detection signal, in particular, on the radiation flux, can be predefined and can be stored in a look-up table. This dependence can be predefined by using calibration measurements, wherein illumination parameters like the illumination light intensity, the times of illumination light pulses, et cetera are chosen such that for at least one given respective parameter of the radiation source like the radiation flux and/or for the respective generated detection signal the polarization reduction is maximized.

It is further preferred that the detector comprises a polarization degree determination unit for determining a polarization degree value being indicative of a degree of polarization of the direct conversion material, wherein the illuminator is adapted to illuminate the direct conversion material depending on the polarization degree value. In particular, the polarization degree determination unit is adapted to measure the time needed by electrons to move from the cathode to the anode and to determine the polarization degree value depending on the measured time. For instance, the polarization degree determination unit can be adapted to determine a polarization degree value indicating a larger polarization, if the measured time, which can be regarded as being a time-of-flight, is longer, and to determine a polarization degree value indicating a smaller polarization, if the measured time is smaller. For measuring the time-of-flight the cathode is preferentially illuminated with visible light generating electrons only close to the cathode. Thus, for defining the generation time, at which the electrons are generated at the cathode, the time of emitting the illumination light can be provided by the illuminator, wherein this generation time can be used together with the time of arrival of the electrons at the anode as measured by the detection signal generator for determining the time-of-flight and, thus, the polarization degree value. The degree of polarization of the direct conversion material can therefore be determined, without necessarily requiring additional components for measuring the polarization. Moreover, by illuminating the direct conversion material depending on the determined polarization degree value, the illumination by the illumination light can be adapted to the actual present polarization within the direct conversion material, which allows for a further improved illumination and, thus, a further improved polarization reduction.

In a preferred embodiment the detector further comprises a detection value determining unit for determining detection values being indicative of the radiation depending on the generated detection signal and a detection value correction unit for correcting the detection values depending on the illumination of the direct conversion material by the illumination light. The illumination of the direct conversion material by the illumination light may adversely affect the detection values, which should be indicative only of the radiation to be detected and which should not be indicative of the illumination light. By correcting these detection values depending on the illumination of the direct conversion material by the illumination light, a generally possible contribution of the illumination light to the determined detection values can be reduced or removed from the detection values, thereby improving the quality of the detection values.

In a further aspect of the present invention a projection data generation system for generating projection data of an object is presented, wherein the system comprises:
  a radiation source for providing radiation for traversing the object,
  a detector as defined in claim 1 for detecting the radiation, after having traversed the object, for generating a detection signal depending on the detected radiation and for generating the projection data depending on the generated detection signal.

The projection data generation system is preferentially further adapted to reconstruct an image of the object from the projection data. The projection data generation system may therefore further be regarded as being an imaging system like a computed tomography system or a nuclear imaging system like a positron emission tomography system or a single photon emission computed tomography system. However, the projection data generation system can also be another system for generating projection data like an x-ray C-arm system. The projection data generation system is preferentially adapted such that it is rotatable around the object, in order to acquire projection data in different acquisition directions. Projection data acquired in different acquisition directions may be used for reconstructing an image of the object by using, for instance, reconstruction techniques like a back projection technique.

In an embodiment the projection data generation system may comprise a rotor, which is rotatable with respect to a stator, wherein the radiation source and the anode, the cathode and the direct conversion material of the detector are mounted on the rotor and the illuminator of the detector is mounted on the stator, wherein the illuminator is adapted to illuminate an entire circular region of the projection data generation system, through which the cathode is moved while being rotated. Moreover, in the same or in another embodiment, the projection data generation system may comprise several detectors, which may also be regarded as being detector sub units, wherein the illuminators of the detectors are adapted to illuminate the direct conversion material of the respective detector by the illumination light depending on the generated detection signal of the respective detector and/or depending on the radiation emitted by the radiation source, wherein for at least two of the detectors the dependences of the illumination on the generated detection signal and/or on the radiation emitted by the radiation source are different. This may allow for a control of the illumination depending on the radiation flux obtained from the generated detection signal and/or the radiation source. Moreover, since this dependence may be different for different detectors of the projection data generation system, detectors, which are generally expected to receive a larger radiation flux, can be handled differently in comparison to detectors, which are expected to receive a lower radiation flux. Since the degree of polarization depends on the radiation flux, this adaptation of the illumination to the radiation flux conditions can further improve the polarization reduction.

In a further aspect of the present invention a detection method for detecting radiation by using a detector as defined in claim 1 is presented, wherein the detection method comprises:
  converting radiation into electrons and holes by an intermediate direct conversion material arranged between an anode and a cathode, wherein the electrons are collected by the anode,
  generating a detection signal depending on the collected electrons by a detection signal generator,
  illuminating the direct conversion material with illumination light being broadband visible and/or broadband infrared light by an illuminator.

In a further aspect of the present invention a projection data generation method for generating projection data of an object is presented, wherein the method comprises:
  providing radiation for traversing the object by a radiation source,
  detecting the radiation, after having traversed the object, and generating a detection signal depending on the detected radiation by a detector as defined in claim 1,
  generating the projection data depending on the generated detection signal.

In a further aspect of the present invention a detection computer program for detecting radiation is presented, wherein the detection computer program comprises program code means for causing a detector as defined in claim 1 to carry out the steps of the detection method as defined in claim 12, when the computer program is run on a computer controlling the detector.

In a further aspect of the present invention a projection data generation computer program for generating projection data of an object is presented, wherein the computer program comprises program code means for causing a projection data generation system as defined in claim 11 to carry out the steps of the projection data generation method as defined in claim 13, when the computer program is run on a computer controlling the projection data generation system.

It shall be understood that the detector of claim 1, the projection data generation system of claim 11, the detection method of claim 12, the projection data generation method of claim 13, the detection computer program of claim 14 and the projection data generation computer program of claim 15 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings:

FIGS. 5 and 6 and FIGS. 7 and 8 show schematically and exemplarily further embodiments of a detector, FIGS. 9 and 10 illustrate schematically and exemplarily a further embodiment of a projection data generation system, FIG. 11 shows schematically and exemplarily generated electrons and holes near a cathode of a detector, FIGS. 13 and 14 show schematically and exemplarily a further embodiment of the detector.

DETAILED DESCRIPTION OF EMBODIMENTS

Figure 1:
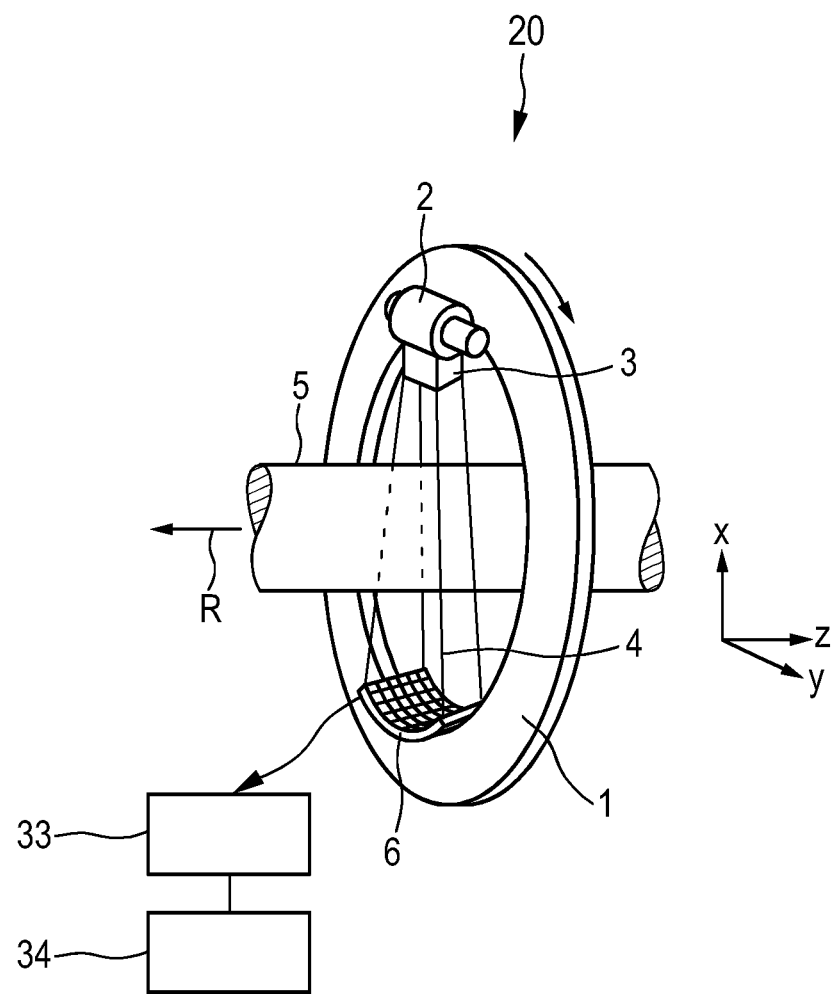
FIG. 1 shows schematically and exemplarily an embodiment of a projection data generation system.

FIG. 1 shows schematically and exemplarily an embodiment of a projection data generation system 20 for generating projection data of an object. In this embodiment the projection data generation system is a computed tomography system. The computed tomography system 20 includes a gantry 1, i.e. a rotor, which is capable of rotation with respect to a stator (not shown in FIG. 1) about a rotational axis R which extends parallel to the z direction. A radiation source 2 being, in this embodiment, an x-ray tube is mounted on the gantry 1. The radiation source 2 is provided with a collimator 3, which forms, in this embodiment, a conical radiation beam 4 from the radiation generated by the radiation source 2. The radiation traverses the object (not shown), such as a patient, in an examination zone 5. After having traversed the examination zone 5 the radiation beam 4 is incident on a detector 6 mounted on the gantry 1.

The detector 6 is adapted to generate a detection signal depending on the detected radiation and to generate the projection data, i.e. detection values, depending on the generated detection signal. While detecting the radiation the gantry 1 rotates around the examination zone 5 such that the projection data can be acquired in different acquisition directions. The projection data are provided to a reconstruction unit 33 for reconstructing an image of the object, which can be shown on a display 34. The reconstruction unit 33 can use known computed tomography reconstruction algorithms like a filtered back projection algorithm, a Radon inversion algorithm, et cetera.

Figure 2:
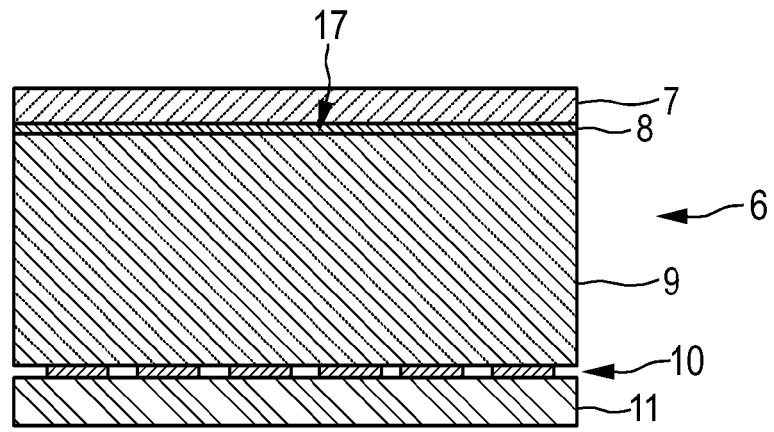
FIG. 2 shows schematically and exemplarily an embodiment of a detector of the projection data generation system.

FIG. 2 shows schematically and exemplarily an embodiment of the detector 6 in more detail. The detector 6 comprises an anode 10, a cathode 8 and an intermediate direct conversion material 9 for converting the radiation 4 into electrons and holes, wherein the electrons are collected by the anode 10. The anode 10 is preferentially pixelated, in order to collect the electrons spatially resolved. The detector 6 further comprises a detection signal generator 11 for generating a detection signal depending on the collected electrons and an illuminator 7 for illuminating the direct conversion material 9 with illumination light being broadband visible light in this embodiment. The detection signal generator 11 can further be adapted to determine a detection value depending on the generated detection signal. For this purpose the detection signal generator 11 can comprise a correspondingly adapted application-specific integrated circuit (ASIC). The intermediate direct conversion material 9 is a direct conversion crystal like a CdTe crystal or a CZT crystal.

The illuminator 7 and the cathode 8 are adapted such that the direct conversion material 9 is illuminated by the illumination light through the cathode 8. In this embodiment, the cathode 8 is continuous over the whole incidence surface 17 of the direct conversion crystal 9, through which the x-ray radiation enters the direct conversion crystal 9, and transparent to the illumination light. The cathode 8 comprises, for instance, indium tin oxide (ITO) or another electrically conductive material, which is transparent to the broadband visible illumination light.

In this embodiment the illuminator is a light source 7 emitting the illumination light substantially homogeneously into the direct conversion crystal 9. Preferentially, the light source 7 is an OLED, which is isolated from the high voltage applied to the anode and the cathode. In a further embodiment, the light source 7 and the cathode 8 can be configured such that the cathode 8 may also be used as an electrode layer of the OLED 7, wherein the OLED 7 comprises this electrode layer 8, a further electrode layer and organic material between these two electrode layers and wherein the illumination light is emitted into the direct conversion crystal 9, if a voltage is applied to the electrode layers of the OLED 7. In a further embodiment the detector may comprise a cathode with openings, through which the direct conversion crystal is illuminatable by the illumination light, as will be described in the following with reference to FIGS. 3 to 8.

Figures 3, 4:
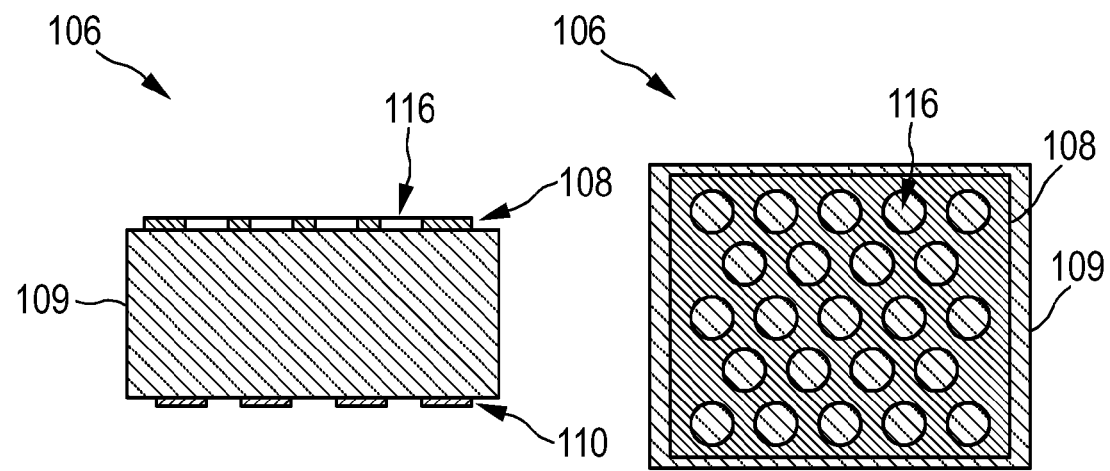
FIGS. 3 and 4 show schematically and exemplarily components of a further embodiment of a detector.

FIG. 3 shows schematically and exemplarily a side view and FIG. 4 shows a top view of some components of a detector 106 schematically and exemplarily shown in FIGS. 5 and 6. In particular, FIGS. 3 and 4 show a direct conversion crystal 109 with a perforated cathode 108 having openings 116 and a pixelated anode 110.

FIG. 5 shows schematically and exemplarily a side view and FIG. 6 shows schematically and exemplarily a top view of the detector 106. The illuminator of the detector 106 comprises a diffractive plate 112 with optical structures 114, which can also be regarded as being macro structures, and light sources 113 for providing the illumination light 115 to be coupled relatively homogeneously through a side surface of the diffractive plate 112 into the diffractive plate 112 by using a coupling element 120. The illumination light 115 is coupled out at the optical structures 114. The optical structures 114 and the openings 116 in the cathode 108 are aligned with each other such that the illumination light coupled out of the diffractive plate 112 traverses the cathode 108, in order to illuminate the direct conversion crystal 109. The diffractive plate 112 and the cathode 108 are arranged on an incidence surface 117 of the direct conversion crystal 109, through which the x-ray radiation to be detected enters the direct conversion crystal 109. Moreover, also in this embodiment a detection signal generator 111 generates a detection signal depending on electrons collected by the anode 110 and generates detection values depending on the generated detection signal.

FIG. 7 shows schematically and exemplarily a side view of a further embodiment 206 of a detector and FIG. 8 shows schematically and exemplarily a top view of this detector. Also this detector comprises a cathode 208 with openings 216 on an incidence surface 217 of a direct conversion crystal 209 and a pixelated anode 210. Moreover, also in this embodiment the detector 206 comprises a detection signal generator 211 for generating a detection signal depending on electrons collected by the pixelated anode 210 and for generating detection values depending on the generated detection signal. Moreover, also in this embodiment the illuminator comprises light sources 213. However, in comparison to the embodiment described above with reference to FIGS. 5 and 6, in this embodiment the illuminator comprises a diffuser plate 212 instead of a diffractive plate 112. The light 215 provided by the light sources 213 is coupled into the diffuser plate 212 by using a coupling element 220, where it is coupled out by micro structures into the direct conversion crystal 209. The diffuser plate and the diffractive plate are preferentially both transparent to x-ray radiation. Moreover, the cathode can be made of a material being transparent to the illumination light provided by the light sources. In order to provide a transparent cathode in these embodiments of the detector and also in other embodiments, it can made of ITO, fluorine-doped tin oxide (FTO), ZnO:Al, tin metal layers, or other conductive materials being transparent to the illumination light. In particular, materials originating from the light emission device (LED) industry and/or the solar cell industry can be used for providing the transparent cathode material.

The projection data generation system can comprise several of the described detectors. Thus, the projection data generation system can comprise a detection device including several of the detectors, for instance, of the detectors described above with reference to FIGS. 2 to 8. A projection data generation system with a detection device comprising several detectors will in the following be described with reference to FIGS. 9 and 10.

FIG. 9 shows schematically and exemplarily the same projection data generation system 320 in two different directions, i.e. FIG. 9 illustrates an x-y plane and FIG. 10 illustrates an y-z plane. The projection data generation system 320 comprises an x-ray radiation source 302 for providing x-ray radiation 304 traversing an object 321. After having traversed the object 321, the x-ray radiation 304 is detected by detectors 306. Each detector 306 comprises an anode, a cathode, an intermediate direct conversion material and a detection signal generator, which are indicated in FIGS. 9 and 10 by the box 318. The cathode, the anode, the direct conversion material and the detection signal generator can be similar to the corresponding elements described above with reference to FIGS. 2 to 8. Thus, for instance, also in this embodiment the cathode is transparent to illumination light and/or comprises openings. Each detector 306 further comprises an illuminator being, in this embodiment, a light source 313. In particular, also in this embodiment the direct conversion material comprises an incidence surface, through which the radiation to be detected enters the direct conversion material, wherein the cathode is arranged on the incidence surface and wherein the illuminator 313 is adapted such that the direct conversion material is illuminated by the illumination light in an illumination direction being inclined with respect to the incidence surface 317. Thus, in this embodiment the illumination direction is not parallel and not perpendicular to the incidence surface 317.

The detectors 306 form two rows, wherein each row is arranged in a bow of the projection data generation system. Laterally from each pair of direct conversion crystals with the anode, the cathode and the detection signal generator, i.e. to the left and to the right in FIG. 10, separate light sources 313 are provided. Thus, the projection data generation system 320 shown in FIG. 9 and FIG. 10 comprises separate light sources 313 in two rows along the bow of the detector array formed by the detectors 306.

Since the illuminator 313 is a separate element such that it is movable with respect to, for instance, the anode, the cathode and the direct conversion material, the radiation source, the anode, the cathode and the direct conversion material can be mounted on a rotor of the projection data generation system and the separate illuminator of the detector can be mounted on a stator of the projection data generation system, wherein the illuminator 313 can be adapted to illuminate an entire circular region of the projection data generation system, through which the cathode is moved while being rotated. Also in other embodiments the illuminator can be separate from other components of the detector like the cathode, the direct conversion material, the anode and the detection signal generator. For instance, with respect to the embodiments described above with reference to FIGS. 5 to 8, the diffractive plate or the diffuser plate, respectively, can be mounted onto an inner side of the gantry. Thus, the inner side of the gantry can be covered with a diffusive and/or diffractive material, which may be substantially ring shaped, such the illumination light coupled into the diffusive and/or diffractive material is diffused and/or diffracted to the full inner side of the gantry. The direct conversion material rotates within the gantry and is thereby illuminated by the diffused and/or diffracted light.

CdTe and CZT are wide band gap semiconductor materials that are well suited for manufacturing of x-ray detectors, in particular, high-flux x-ray detectors, for astrophysical and medical applications. These types of detectors are very important in applications like solid-state nuclear medicine systems and spectral computed tomography systems. These applications are based on single photon x-ray counting.

The performance of known CdTe and CZT detectors is often critically affected by charging of the bulk material of the detector, which causes build-up of an internal electric field and counteracts the applied bias voltage. This effect is known as polarization of the detector. Polarization especially occurs under high flux x-ray exposure conditions and strongly limits the performance of, for example, spectral computed tomography photon counting, for instance, the pulse widths may vary with exposure resulting in a not time-stable spectral response.

In order to increase the allowed dose, it would be possible to illuminate a CdTe or CZT crystal with infrared light having one or several certain wavelengths. This infrared light is absorbed only by certain charged defects, which are mainly trapped holes. After absorption of light these will by detrapped, reducing the amount of charge in the system and postponing polarization. Alternatively, the crystal might be heated. In both cases, however, the holes, which are by a factor of 20 to 50 slower drifting than electrons, will not be removed, but freed to be just trapped again on their way to the cathode, such that the positive charge remains for a relative long time within the crystal. Another preferred way is a cancellation of holes by recombination with fast electrons. For this an ohmic contact like indium could be used which may inject a relatively large electron density near the cathode such that holes, which are mainly trapped holes, are removed by electron/hole recombination. This technique however has the disadvantage that electrons are permanently injected causing relative high offset currents which are therefore timely varying with the exposure and which degrade the performance of readout electronics.

To suppress polarization of the detector under high flux conditions it may be advantageous to provide electrons near the cathode only if needed, i.e. in cases of high exposure. Even better, the required electrons may be injected as controlled pulses within very short time intervals in which the detector might regularly pause from photon counting. The detector described above with reference to FIGS. 1 to 10 may therefore comprise a special configuration of the cathode electrode with broadband visible illumination light, which allows temporal injection of electrons and thereby neutralization of hole traps that cause polarization. Due to the low energy of the illumination light, i.e. due to the energy being much lower than the energy of x-ray radiation, the absorption is mainly in the first micrometers of the direct conversion material. This creates the electrons, which will migrate to the hole traps under the applied field, and also holes within the direct conversion material as schematically and exemplarily illustrated in FIG. 11, in which the electrons and holes are denoted by 40. This differs from the use of infrared light having one or several certain wavelengths only, as the infrared light with these one or several certain wavelengths is directly absorbed by the defects to free holes, while, if broadband visible light is used, the trapped holes are not freed, but directly annihilated by large densities of free electrons.

The detectors described above with reference to FIGS. 1 to 10 may comprise, for instance, a CZT crystal provided with a transparent and/or perforated electrode pattern at the cathode side and a pixelated electrode pattern at the anode side. Preferentially, for both sides a metal is chosen with a high potential barrier towards CZT like platinum, in order to provide blocking contacts. In an embodiment, an electrical insulator may be arranged between the cathode and the direct conversion material, wherein the electrical insulator is preferentially relatively thin, i.e. it may have a thickness between 1 nm to 1 μm. This can lead to low current levels, wherein still enough electrons can be injected through the electrical insulator to reduce polarization.

An absorbed x-ray photon generates a cloud of electron-hole pairs within the CZT crystal, wherein due to the electric field the electrons drift towards the anode and are collected by the read-out chip, i.e. by the detection signal generator. In this way the energy of each incident photon is registered. The holes drift towards the cathode. Holes are much slower than electrons and can be trapped easily in hole traps. This causes the polarization of the detector and occurs especially under high flux x-ray exposure conditions. Polarization can lead to a complete failure of the photon counting technique at high fluxes.

The polarization can be suppressed by neutralizing the trapped holes. This can be achieved by temporal injection of electrons at the cathode side. Under normal operation conditions the cathode contact is blocking or semi-injecting, which results in a low or medium current level, which may be a dark current level or a current level under, for instance, x-ray radiation and which allows accurate energy discrimination. Temporal injection of electrons is preferentially initiated by a short pulse of visible broadband illumination light through the specially designed cathode, which is transparent to the illumination light and/or perforated. The absorption of the illumination light occurs in the first micrometers of the detector and will create holes and electrons nearby the cathode, wherein the applied electric field will force the electrons to move into the direct conversion material. Once the electrons have been forced into the direct conversion material, they can neutralize the trapped holes. This in turn suppresses polarization of the detector. On the other hand, the generated holes near the cathode can be easily collected by the cathode as they typically have to drift only few hundred nanometers such that the probability of hole trapping is very low.

For injecting the electrons the illuminator can be adapted to illuminate the direct conversion material in a pulsed mode. By synchronizing the read-out electronics, i.e. the detection signal generator, with the polarization suppression light pulse, i.e. with the pulsed illumination light, it can be ensured that the injected electrons are not counted. Thus, the illuminator and the detection signal generator may be adapted such that at a time either the direct conversion material is illuminated by the illumination light or a detection signal being indicative of the x-ray radiation is generated.

For a given x-ray exposure dose parameters of the pulsed illumination light can be predefined and stored, for instance, in a look-up table, wherein in operation the illumination by the illumination light can be controlled in accordance with parameters obtained from the look-up table. The parameters, which may be stored in a look-up table, may be the pulse time, the duty cycle and the intensity of the pulsed illumination light. These parameters may be determined in a calibration procedure, in which for different x-ray exposure doses and parameters of the illumination light the polarization is measured and wherein for a respective x-ray exposure dose the parameters of the illumination light are selected, for which the suppression of the polarization was maximized. Thus, in a simple case the pulse parameters may be chosen statically, i.e. a well-defined pulse may be regularly applied during a detector pause, i.e. if the detection signal generator does not generate a detection signal being indicative of the x-ray radiation. However, in an embodiment the detector may also comprise a polarization degree determination unit for determining a polarization degree value being indicative of a degree of polarization of the direct conversion material, wherein the illuminator may be adapted to illuminate the direct conversion material depending on the polarization degree value. For instance, the polarization degree determination unit can be adapted to measure the time needed by electrons to be collected by the anode and to determine the polarization degree value depending on this measured time. For instance, the time of applying the illumination light pulse to the cathode for injecting electrons and the time of detecting these electrons at the anode can be used for determining the time-of-flight of these electrons, wherein the polarization degree value can be determined depending on this time-of-flight of the electrons. The polarization degree determination unit can be adapted to determine a polarization degree value indicating an increased polarization with an increased time-of-flight. The dependence of the polarization degree value on the time-of-flight and the dependence of the parameters of the illumination light pulse on the polarization degree value can be predetermined by calibration measurements, wherein for a given time-of-flight the parameters of the illumination light are determined such that the suppression of the polarization is maximized. The polarization degree determination unit can be adapted to directly provide the time-of-flight value as the polarization degree value or it can be adapted to provide another polarization degree value, which depends on the time-of-flight and which is indicative of the degree of polarization of the direct conversion material. If the polarization degree determination unit provides directly the time-of-flight value as the polarization degree value, it is just required to provide a dependency between the time-of-flight measurements and the parameters of the illumination light. These dependencies can be stored in look-up tables and they can be used to adapt the parameters of the illumination light pulse to the actual polarization of the direct conversion material.

The detector may be used in a synchronous manner to the illumination light pulse such that it measures the time-of-flight of the electrons which are created by the illumination light pulse. This way it is possible to determine the degree of polarization, wherein it is expected that increased polarization will result in a prolonged time-of-flight. For example, by detecting a prolonged time-of-flight, the time and/or intensity of a subsequent illumination light pulse can be adapted such that by generation of more electrons the polarization gets stronger suppressed.

The parameters of the illumination light are preferentially optimized for maximizing the polarization suppression. In particular, the wavelength region of the broadband illumination light and/or the timing of the illumination light pulses may be optimized. For instance, the illumination light pulse may have a temporal duration within the range of 100 ps to one or several µs, further preferred within the range of 100 ps to 10 ns and even further preferred within the range of 100 ps to 1 ns. Many electrons may be injected and then slowed down under "standard" field conditions so that they have time for recombining with trapped holes. This may avoid long dead times of the detector. Moreover, a maximum time, after which such an illumination light pulse, which may also be regarded as being a reset pulse, should be applied, can be defined as a parameter of the illumination light. This maximum time can depend on the x-ray radiation. For instance, a look-up table can be used, which defines this maximum time, which can also be regarded as being a time for a reset, depending on one or several parameters of the x-ray radiation like the x-ray flux. For determining the x-ray flux the detection signal generated by the detection signal generator may be used. However, it is also possible to use the x-ray flux emitted by the x-ray source and to then use different dependencies between the x-ray flux and the maximum time, i.e. to use different look-up tables, for different detectors of a detection device. For instance, if it is known that some detectors of the detection device are arranged such that they will generally receive a lower x-ray flux than other detectors, the dependencies between the x-ray flux emitted by the x-ray source and the maximum time can be such that in low-flux regions the maximum time is larger than in high-flux regions of the detection device.

Although in above described embodiments the illuminator is adapted to illuminate the direct conversion material with pulsed light, the illuminator can also be adapted to modulate the intensity of the illumination light in another way. For instance, the illuminator can be adapted to continuously illuminate the direct conversion material with illumination light having a varying intensity. Also in this case the parameters of the illumination light can depend on, for instance, the current degree of polarization. Moreover, the illuminator can be adapted to illuminate the direct conversion material depending on an expected degree of polarization. For instance, the expected degree of polarization can be determined depending on the future x-ray radiation to be applied, i.e., for instance, on the x-ray radiation of a next cycle, wherein a look-up table may be used comprising assignments between parameters of x-ray radiation like the x-ray intensity or x-ray energy and the expected degree of polarization for determining the expected degree of polarization.

The detectors described above with reference to FIGS. 1 to 10 may further comprise a detection value correction unit for correcting the detection values depending on the illumination of the direct conversion material by the illumination light. For instance, the detection values may be corrected depending on the rate of illumination light pulses, in order to improve the quality of the detection values.

The control of the illuminator and the determination of the corrected detection value will in the following exemplarily be described with reference to FIG. 12.

Figure 12:
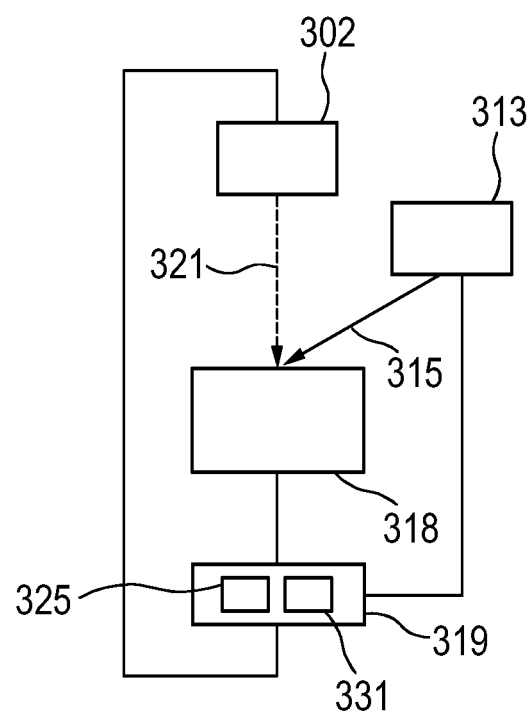
FIG. 12 illustrates schematically and exemplarily an embodiment of a control of an illuminator of the detector.

FIG. 12 shows schematically the illuminator 313, the x-ray source 302 and the box 318 representing the direct conversion material with the cathode and the anode and with the detection signal generator. A controller 319 comprises the polarization degree determination unit 325 and the detection value correction unit 331. The controller 319 is adapted to control the illuminator 313 and to receive from the x-ray source 302 information regarding the emitted x-ray radiation 321 like the emitted x-ray flux. For determining the degree of polarization the controller 319 can be adapted to initiate an illumination light pulse 315 to be applied to the cathode, in order to generate electrons near the cathode, and to determine the time between the initiation of this illumination light pulse and the detection of the generated electrons at the anode for determining the time-of-flight, which can be used for determining the polarization degree value. The controller 319 can then further be adapted to control the parameters of one or several subsequent illumination light pulses depending on the actually determined polarization degree value.

The controller 319 can be integrated with the detection signal generator or it can be a separate element, which, for instance, may not be located on a rotor of a computed tomography system. Moreover, the polarization degree determination unit and/or the detection value correction unit may not be part of the controller, but may be separate units, which may communicate with each other and/or the controller.

Although in the previously described embodiments the illumination light is pulsed, the illumination light can also be continuous light. Moreover, although in the previously described embodiments the illumination light is broadband visible light, the illumination light can also be broadband infrared light. If broadband infrared light is used, it can cause two effects within the direct conversion material. The broadband infrared illumination of the direct conversion material can heat the direct conversion material, wherein the heat can lead to preventing or postponing the polarization. Moreover, the broadband infrared illumination can directly excite trapped holes, in particular, deep level trapped holes, at any and all different trap levels and not only at prior known specific trap levels. By a recombination of these traps the polarization can be prevented or postponed. Both effects in combination lead to a very efficient polarization suppression. The above described embodiments, in particular, the embodiments described above with reference to FIGS. 1 to 10, can therefore also be used by applying broadband infrared illumination light to the direct conversion material. In this case the cathode should be transparent to infrared light. The embodiments can also be adapted to apply a combination of broadband visible light and broadband infrared light.

Since the broadbandness of the infrared illumination ensures that holes trapped at a lot of different trap levels are excited and detrapped, it is not necessary to investigate the trap levels, which may be very difficult and which is likely unstable, and to match specific infrared wavelengths to the discovered trap levels, which is generally also very difficult, as would be required by the specific wavelengths infrared technique disclosed in the above mentioned prior art document.

Thus, the broadband infrared light does not only comprise one or several specific wavelengths, but it comprises a broad band of wavelengths, in order to perform detrapping of multiple deep and shallow traps due to the spectrum. Moreover, the broadband infrared light is used to preferentially substantially homogeneously heat the direct conversion material, wherein an insulating layer may be placed on the cathode to prevent a gradient in the direct conversion material. The insulating layer can prevent cooling, i.e. the direct conversion material may be heated to higher temperatures, and increase the homogeneity of the heating.

The use of the broadband infrared light allows for a combination of direct detrapping by trap excitation and indirect detrapping by heating of the direct conversion material. A part of the broadband infrared light can also be used to indirectly heat the direct conversion material for causing an indirect detrapping of holes. For instance, the broadband infrared light can be used to increase the temperature within the gantry by directly heating parts of the system not being the direct conversion material, wherein the generated heat indirectly heats the direct conversion material. To incorporate the broadband infrared light illumination in an imaging system like a computed tomography system infrared light guides like the above described diffractive and diffuser plates may be used.

Although in above described embodiments certain ways of illuminating the direction conversion material with broadband visible light and/or broadband infrared light have been described, in other embodiments the illumination can also be provided in another way. For instance, the detector can be covered with a filter which allows only a broadband visible part and/or a broadband infrared part of light having a broader spectrum provided by a light source to reach the direct conversion material. If several detectors, which may be regarded as being sub detectors, are present, which form a bow of detectors, this bow may be covered by a corresponding curved filter.

Although in above described embodiments the illuminator illuminates the direct conversion material by the illumination light through the cathode, in another embodiment the illuminator can be adapted to illuminate the direct conversion material through another surface of the direct conversion material. For instance, as schematically and exemplarily illustrated in FIGS. 13 and 14, the direct conversion material can be illuminated through a side surface not covered by the cathode and the anode. FIG. 13 illustrates a side view and FIG. 14 illustrates a top view. The detector 406 shown in FIGS. 13 and 14 comprises a direct conversion material 409, a cathode 408, a pixelated anode 410 and a detection signal generator 411. Moreover, the illuminator comprises several light sources 413 for providing the illumination light. The direct conversion material 409, the pixelated anode 410, the detection signal generator 411 and the light sources 413 can be similar to the corresponding components of the detectors described above with reference to FIGS. 1 to 10. However, in this embodiment the cathode 408 does not need to be transparent to the illumination light provided by the light sources 413, because the illumination light 415 is coupled into the direct conversion material 409 through a side surface not covered by the cathode 408. For coupling the illumination light 415 into the direct conversion material 409 a coupling element 420 may be used.

The broadband visible light has preferentially a broadness which is larger than 100 nm, further preferred larger than 200 nm and even further preferred larger than 300 nm. This broadness may be smaller than 500 nm. The broadband infrared light has preferentially a broadness which is larger than 100 nm, further preferred larger than 200 nm and even further preferred larger than 300 nm. The broadband visible light is preferentially within a wavelength range of 380 nm to 780 nm. It can cover this entire visible wavelength range or only a part of the visible wavelength range. The broadband infrared light is preferentially within a wavelength range of 780 nm to 1 mm and further preferred within a wavelength range of 780 nm to 15 µm. The broadband infrared light can cover the entire respective wavelength range or only a part of the respective wavelength range.

Figure 15:
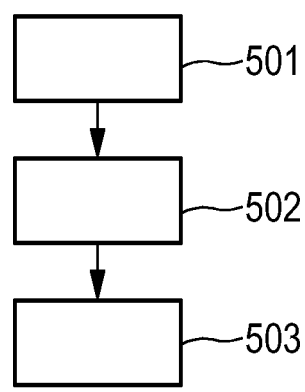
FIG. 15 shows a flowchart exemplarily illustrating an embodiment of a projection data generation method for generating projection data of an object.

In the following an embodiment of a projection data generation method for generating projection data of an object will exemplarily be described with reference to a flowchart shown in FIG. 15.

In step 501 the radiation source provides radiation for traversing the object. In step 502 the radiation is detected, after having traversed the object, and a detection signal is generated depending on the detected radiation by at least one of the above described detectors. The detection process includes converting the radiation into electrons and holes by the direct conversion material arranged between the anode and the cathode, wherein the electrons are collected by the anode, generating a detection signal depending on the collected electrons by the detection signal generator and illuminating the direct conversion material with illumination light being broadband visible and/or infrared light by the illuminator. The illumination of the direct conversion material is preferentially performed, when the detection signal generator does not generate a detection signal, i.e. the illumination of the direct conversion material by the illumination light and the generation of the detection signal are preferentially synchronized such that the direct conversion material is illuminated by the illumination light only in a detector pause, in which the detection signal is not generated. In step 503 the projection data, i.e. detection values, are generated depending on the generated detection signal.

The conversion of the radiation into electrons and holes, the generation of the detection signal and the illumination of the direct conversion material by the illumination light performed in step 102 can be regarded as being steps of a detection method for detecting radiation. Moreover, the projection data generation method can comprise further steps like rotating the radiation source and the detector around the object for acquiring the projection data in different directions, wherein these projection data can be used for reconstructing a computed tomography image, which may be shown on a display.

Although certain materials, configurations, techniques for reducing the polarization, et cetera have been described above, the detector can also comprise other materials and configurations and can provide other techniques for reducing polarization by illuminating the direct conversion material with broadband visible and/or infrared light. For instance, instead of CZT another direct conversion material can be used by the detector. The light sources of the illuminator are preferentially broadband LEDs. However, also other light sources can be used for illuminating the direct conversion material with the broadband visible and/or infrared light like broadband OLEDs, hot filaments light sources, thin film light sources et cetera.

Although in above described embodiments the detector is adapted to detect x-ray radiation, the detector can also be adapted to detect another kind of radiation like gamma radiation. In fact, the detector is preferentially adapted to be used in an x-ray imaging system or a nuclear imaging system, wherein the detector detects x-ray radiation or gamma radiation, respectively.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of a polarization degree value, the determination of a time-of-flight, the generation of a detection signal, the determination of a detection value, the correction of the detection value, et cetera performed by one or several units or devices can be performed by any other number of units or devices. These procedures and/or the control of the projection data generation system in accordance with the projection data generation method and/or the control of the detector depending on the detection method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a detector for detecting radiation, especially x-ray radiation used in a computed tomography system. The detector comprises a direct conversion material for converting radiation into electrons and holes, which are used for generating an electrical detection signal. The direct conversion material is illuminated with illumination light being broadband visible and/or broadband infrared light for reducing, in particular, eliminating, a polarization of the direct conversion material, which may occur when being traversed by the radiation to be detected and which may reduce the detection performance. By reducing the polarization of the direct conversion material the detection performance can be improved.

This invention claimed is:

1. A detector for detecting radiation, the detector comprising:
    an anode, a cathode and an intermediate direct conversion material for converting radiation into electrons and holes, wherein the electrons are collectable by the anode, the intermediate direct conversion material is disposed between the anode and the cathode, the intermediate direct conversion material comprises an incidence surface, and the cathode is arranged on the incidenece surface;
    a detection signal generator for generating a detection signal depending on the collected electrons;
    an illuminator for illuminating the intermediate direct conversion material with illumination light being broadband visible and/or broadband infrared light, wherein the illuminator comprises:
        a diffractive plate with macro structures;
        a light source, located outside of the radiation, configured to emit illumination light from outside a path of the radiation; and
        coupling element that couples the illumination light through a side surface of the diffractive plate into the diffractive plate, where the illumination light is coupled out of the macro structures and traverses opening in the cathode to the intermediate direct conversion material; and
    wherein wavelengths of the illumination light include a band of wavelengths at least 100 nm broad.

2. The detector as defined in claim 1, wherein the diffractive plate diffracts the illumination light before traversing the cathode.

3. The detector as defined in claim 1, wherein the illuminator is a separate element such that it is movable with respect to the anode, the cathode and the direct conversion material.

4. The detector as defined in claim 1, wherein the illuminator is adapted to illuminate the direct conversion material in an intensity modulated mode.

5. The detector as defined in claim 1, wherein the illuminator is adapted to illuminate the direct conversion material depending on the generated detection signal.

6. The detector as defined in claim 1, wherein the detector further comprises a polarization degree determination unit for determining a polarization degree value being indicative of a degree of polarization of the direct conversion material, wherein the illuminator is adapted to illuminate the direct conversion material depending on the polarization degree value.

7. The detector as defined in claim 6, wherein the polarization degree determination unit is adapted to measure the time needed by electrons to move from the cathode to the anode and to determine the polarization degree value depending on the measured time.

8. A projection data generation system for generating projection data of an object, the system comprising:
    a radiation source for providing radiation for traversing the object,
    the detector as defined in claim 1 for detecting the radiation, after having traversed the object, for generating a detection signal depending on the detected radiation and for generating the projection data depending on the generated detection signal.

9. A detection method for detecting radiation by using a detector as defined in claim 1, the detection method comprising:
    converting radiation into electrons and holes by the intermediate direct conversion material arranged between the anode and the cathode, wherein the electrons are collected by the anode;
    generating the detection signal depending on the collected electrons by the detection signal generator;
    illuminating the direct conversion material with illumination light being broadband visible and/or broadband infrared light by the illuminator.

10. A projection data generation method for generating projection data of an object, the method comprising:
    providing the radiation for traversing the object by a radiation source;
    detecting the radiation, after having traversed the object;
    generating a detection signal depending on the detected radiation by the detector as defined in claim 1; and
    generating the projection data depending on the generated detection signal.

11. A detection computer program for detecting radiation, the detection computer program comprising program code means for causing a detector as defined in claim 1 to carry out the steps of the detection method, when the computer program is run on a computer controlling the detector.

12. A projection data generation computer program for generating projection data of an object, the computer program comprising program code means for causing a projection data generation system as defined in claim 8 to carry out the steps of the projection data generation method, when the computer program is run on a computer controlling the projection data generation system.

13. The detector as defined in claim 1, wherein the at least one band of the illumination light includes the broadband visible light wavelengths between 380 nm to 780 nm.

* * * * *